United States Patent [19]

Demaline

[11] Plant 5,004

[45] Mar. 22, 1983

[54] FEMALE HOLLY PLANT

[75] Inventor: Lester L. Demaline, Avon, Ohio

[73] Assignee: Willoway Nurseries, Inc., Avon, Ohio

[21] Appl. No.: 263,214

[22] Filed: May 13, 1981

[51] Int. Cl.[3] ..... A01H 5/12

[52] U.S. Cl. ..... Plt./65

[58] Field of Search ..... Plt./65

*Primary Examiner*—Robert E. Bagwill

*Attorney, Agent, or Firm*—Maky, Renner, Otto & Boisselle

[57] ABSTRACT

A female holly plant is disclosed herein having a pyramidal shape and growth habit with abundant and well distributed berries. The new stem and branch growth has dark, blue black bark giving the holly plant a distinctive coloration and appearance.

4 Drawing Figures

1

The present invention and discovery relates to a new and distinct variety of a female ilex or holly plant, selected by me and having unusual and distinctive growth patterns, structural form and appearance.

In particular, my new Ilex exhibits a very vigorous growth pattern, having grown some 18 inches in one year. This Ilex is very pyramidal in growth habit. In the first year of growth, the immature stems and branches have a blue-green bark, with this bark changing to a very dark blue black coloration with additional maturity. In the second year of growth with still further wood maturation, the very dark blue-black bark changes back to approximately the original blue-green coloration. The leaves on this Ilex are medium size and have 9 to 15 spines on the outer perimeter of the leaf. The leaves are very dark green and glossy on the upper side and are a lighter, dull green on the under side. This female Ilex has a deep, orange-red fruit which forms in abundance in November and hangs on the plant until approximately May or June of the following year.

The principal novel and distinctive characteristics of this new Ilex variety are considered to be, in combination:

(1) The over-all structure is very pyramidal in form and growth habit.

(2) The new bark on the stems and branches is dark blue-black in coloration.

(3) The leaf structure of this naturally crossed Ilex is very strong and shapely, resembling a true holly leaf.

(4) The deep orange-red fruit is abundant on the plant until late spring.

My new Ilex has been propagated asexually at Avon, Ohio by rooted cuttings. The original parent specimen was selected by me as a natural cross seedling from a number of seedlings at my nursery. This natural cross seedling from open pollination had the seed taken from an aquifolium female holly parent, with the variety of the male holly parent being unknown.

Referring now more particularly to the drawings:

FIG. 4 shows the fruit or berries on such holly plant.

2

The following is a specific description of such new holly plant based on the ISCC-NBS Centroid Color Code.

Figure 1:
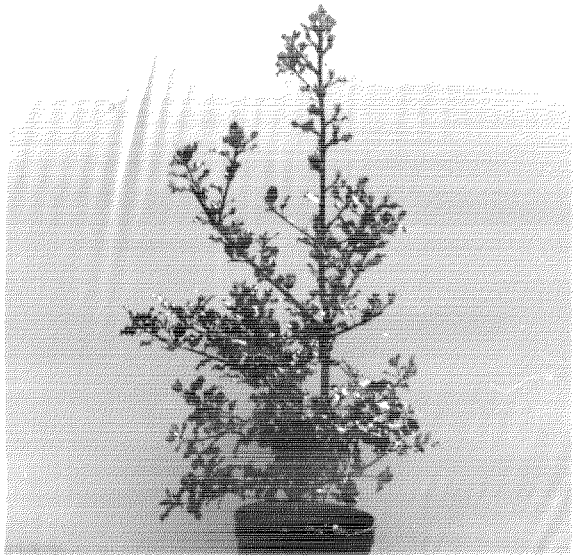
FIG. 1 shows the natural pyramidal shape of such holly plant having a central leader.
Figure 2:
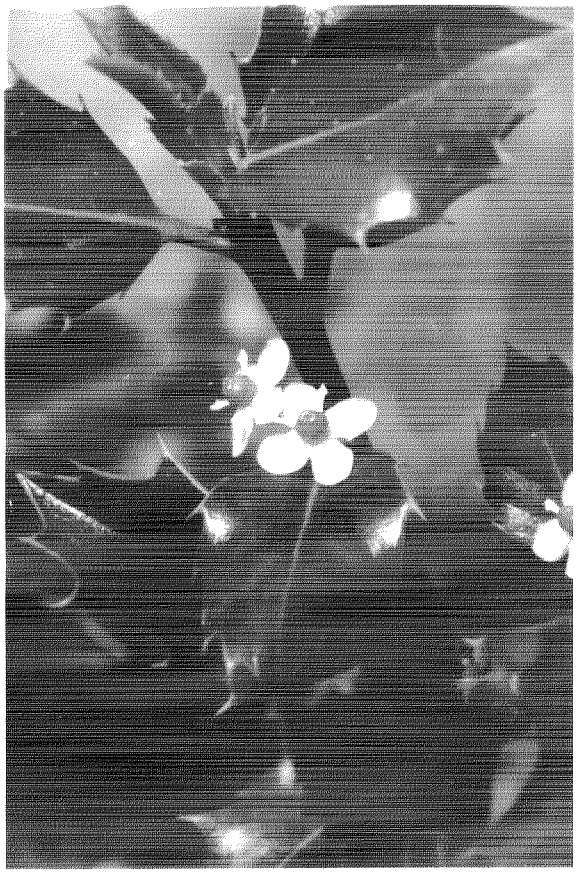
FIG. 2 shows such holly plant in flower and the leaf structure.

As best shown in FIGS. 1 and 2, the new holly plant exhibits a pyramidal growth habit and shape with upright branching and a central leader. The growth pattern is vigorous and visually exposes new stem and branch growth having a very dark, blue-black bark giving the holly plant a unique coloration and appearance. The approximate mature height of my new holly plant is 15 to 20 feet, with the spread at the base being approximately 8 to 10 feet. My originally selected holly plant has grown in Cleveland, Ohio for approximately 10 years, and such plant and its asexually propagated progeny demonstrate cold hardiness not only in Cleveland, Ohio but also in the rest of Zone 5.

Figure 3:
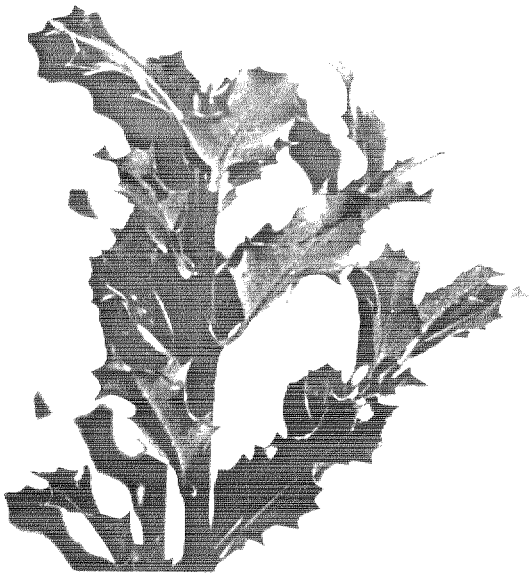
FIG. 3 shows the leaf structure and the very dark blue-black bark of the new stem and branch growth on my holly plant.
Figure 2:
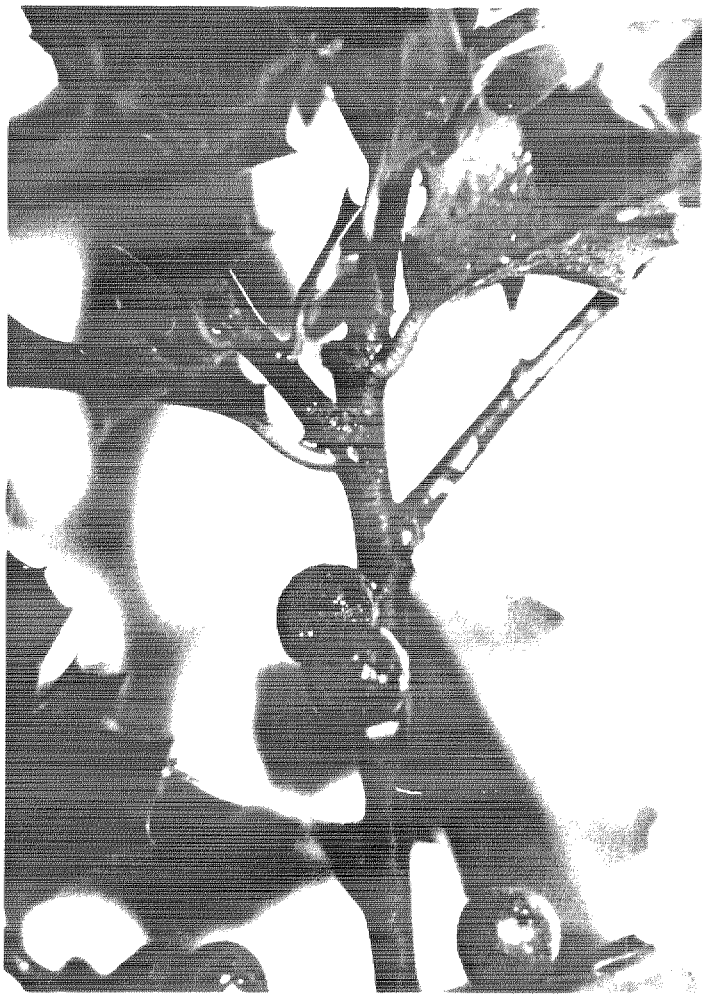

In this regard, the immature stem and branch growth initially has a blue-green coloration (125.M o 1 G and 126.d o LG), but this immature bark color in the new growth changes in approximately three months to a very dark, blue-black (235.p Black) color with maturity as best shown in FIG. 3. The very dark blue-black bark on the new stem and branch growth retains this color for approximately the first growth year and is readily observable as shown in FIGS. 1 and 2 since it is not as fully leafed as the more mature part of the plant. In the second year of growth with additional wood maturation, the bark on the stems and branches changes back to approximately its original blue-green color (125.M o 1 G and 126.d o LG) and retains such color for the life of the plant.

The leaves are of medium size, approximately 30 mm wide and 57 mm in length, and have 9 to 15 spines on their outer perimeter. The leaves are very dark green (147.v.d.G.) and glossy on their upper side and are a lighter dull green (125.m.o lG) on their lower side. The leaves seem to be free of most holly diseases and insects and are very strong and shapely.

In blooming season, the holly plant is in full bloom for approximately two days and the flowers are rather small (approximately 5 mm in length) and relatively inconspicuous on the plant as is demonstrated by FIG. 2. The flower is four petal pure white (white 263.) with a green (117 s YG) stamen and creamy green (121.p.YG) pistil.

The fruit has a desirable size of approximately 10 mm in diameter and is mostly round in shape. As best shown in FIG. 4, the fruit or berries are abundant on and well distributed over the holly plant. The fruit or berry is a very clear orange-red (36. deep r o) (13. deep red) and has a small indentation of gray coloration (265. med.Gy) at its calyx end. The fruit remains on the holly plant until late spring before dropping.

By way of comparison to Ilex × meservae varieties, my holly plant has slightly darker stem coloration, a distinctive branching habit more pyramidal in shape, thicker stems, larger leaves and a lighter leaf coloration. By way of comparison to normal aquifolium varieties, my female holly plant has much darker stem coloration, thicker stems, and similarly sized leaves having darker coloration. My female holly plant is believed to be hardier than most aquifoliums and about the same hardiness as most Ilex × meservae varieties.

I claim:

1. A new and distinct variety of female holly plant, Ilex, substantially as shown and described herein.

* * * * *